United States Patent [19]
Saito et al.

[11] Patent Number: 5,870,926
[45] Date of Patent: Feb. 16, 1999

[54] INFRARED MOISTURE MEASURING APPARATUS AND INFRARED MOISTURE MEASURING METHOD

[75] Inventors: Yasuo Saito; Kenji Konishi; Susumu Uchida, all of Kanagawa; Ryoichi Ishii, Tokyo, all of Japan

[73] Assignee: Japan Tobacco Inc., Minato-ku, Japan

[21] Appl. No.: 816,503

[22] Filed: Mar. 13, 1997

[30] Foreign Application Priority Data

Mar. 15, 1996 [JP] Japan .................................. 8-059134
Dec. 19, 1996 [JP] Japan .................................. 8-339505

[51] Int. Cl.$^6$ .................................................. G01N 21/17
[52] U.S. Cl. ........................ 73/73; 250/339.1; 250/341.8; 250/339.11
[58] Field of Search ................ 73/29.01, 29.02, 73/335.01, 73; 250/339.1–339.11, 339.04, 341.1, 348.1, 351.8

[56] References Cited

U.S. PATENT DOCUMENTS

| | | | |
|---|---|---|---|
| 4,097,743 | 6/1978 | Carlson | 250/339.11 X |
| 4,463,261 | 7/1984 | Bowman | 250/339.1 |
| 4,764,018 | 8/1988 | Inoue | 250/339.1 X |
| 4,996,430 | 2/1991 | Gupta | 250/339.11 |
| 5,210,590 | 5/1993 | Landa et al. | 356/319 |
| 5,220,168 | 6/1993 | Adamski et al. | 250/341.8 X |
| 5,270,546 | 12/1993 | Jamroz et al. | 250/341.8 |
| 5,476,108 | 12/1995 | Dominguez et al. | 131/108 |

FOREIGN PATENT DOCUMENTS

3149869A1 6/1983 Germany .
2098725 11/1982 United Kingdom .

OTHER PUBLICATIONS

Patent Abstracts of Japan, vol. 005, No. 113 (P–089), Nov. 13, 1981; and JP–56–108940 A, published Aug. 28, 1981.

*Primary Examiner*—Michael Brock
*Attorney, Agent, or Firm*—Birch, Stewart Kolasch & Birch,LLP

[57] ABSTRACT

An infrared moisture measuring apparatus includes a first infrared light-emitting diode (LED) for emitting infrared rays of a measuring beam whose infrared absorption varies by the moisture content of an object to be measured and a second infrared LED for emitting infrared rays of a reference beam whose infrared absorption does not substantially vary by the moisture content of an object to measured. Also, an optical system is provided for illuminating the infrared rays of the measuring and reference beams emitted by the first and second infrared LEDs on the object and focusing the infrared rays reflected from the object, and an InGaAs light-receiving device is provided for receiving the infrared rays focused by the optical system and outputting a light-received signal which corresponds to a light quantity of the received infrared rays. The moisture value of the object is obtained based on the light-received signal output from the InGaAs light-receiving device.

13 Claims, 10 Drawing Sheets

INFRARED MOISTURE MEASURING APPARATUS AND INFRARED MOISTURE MEASURING METHOD

FIELD OF THE INVENTION

The present invention relates to an infrared moisture measuring apparatus and an infrared moisture measuring method which illuminate the infrared rays of a measuring beam whose infrared absorption varies by the moisture content of an object to be measured and the infrared rays of a reference beam whose infrared absorption does not substantially vary by the moisture content of an object to be measured to the object to be measured and, based on the reflected light quantities of the infrared rays, measure the moisture value of the moisture content of the object to be measured.

DESCRIPTION OF THE RELATED ART

This kind of conventional infrared moisture measuring apparatus illuminates both the infrared rays of a measuring beam whose infrared absorption varies by the moisture content of an object to be measured and the infrared rays of a reference beam whose infrared absorption does not substantially vary by the moisture content of an object to be measured to the object to be measured. Then, the infrared moisture measuring apparatus calculates, for example, absorbance based on the reflected light quantities of the infrared rays and converts the calculated absorbance to a moisture value to obtain the moisture content of the object to be measured.

To generate a measuring beam and a reference beam, the conventional infrared moisture measuring apparatus is constructed as follows. That is, a filter wheel on which an interference filter is mounted is rotated by a motor, and light from a light source such as a tungsten lamp is illuminated on the interference filter to split it into a measuring beam and a reference beam. Also, a PbS detector is employed as a detecting device which receives reflected infrared rays. Furthermore, the absorption wavelength of moisture that is used, that is, the wavelength of a measuring beam is 1.94 $\mu$m or 1.45 $\mu$m.

The conventional infrared moisture measuring apparatus constructed as described above, however, has the following disadvantages:

(1) Since a motor and a filter wheel with an interference filter mounted thereon are used, there is the disadvantage that the size of the apparatus itself is increased.

(2) Since the maximum rotational speed of the filter wheel is restricted to about 3000 rpm, the apparatus is unsuitable for high-speed sampling.

(3) A tungsten lamp also becomes a heat source, so the internal temperature of the apparatus rises. This temperature rise results in a degradation in the electronic parts. Thus, attention must be paid to an allowable operating environment temperature range.

(4) A tungsten lamp requires considerable consumption power and consequently the lifetime of the lamp is restricted to about 30000 hours.

(5) As the dark resistance value of a PbS detector varies, its sensitivity changes with the passage of time. Also, there is a considerable fluctuation between devices.

(6) The frequency response of the PbS detector is at about 600 Hz, so the PbS detector is unsuitable for high-speed sampling.

(7) The peak of the wavelength of the spectral sensitivity of the PbS detector is at 2.2 $\mu$m, so if a moisture absorption wavelength of 1.94 $\mu$m is used to measure a moisture value, a spectral characteristic (moisture) will be saturated in high-moisture samples. Also, if a moisture absorption wavelength of 1.45 $\mu$m is used to measure a moisture value, sufficient sensitivity will be unobtainable in low-moisture samples.

In addition, the conventional infrared moisture measuring apparatus has a limitation of an object to be measured because its response speed is slow. For example, the conventional apparatus has been employed to measure the moisture value of raw material which is supplied with a conveyor, as in the case of powder particles or tobacco material, and because this kind of raw material continuously flows on a conveyor, an average moisture value of the entire raw material could be obtained even if points of measurement were spaced. However, for objects which are particularly small and flow intermittently like mass produced lot products such as confectionery products or tablets, the conventional apparatus cannot not only accurately obtain the moisture value of each of products but also the average moisture value of all products, because it has a delay of response.

SUMMARY OF THE INVENTION

It is an objective of the present invention to provide an infrared moisture measuring apparatus where high-speed sampling, i.e., high-speed response is possible and which can achieve device compactness, enhancements in the maintenance and allowable operating environment temperature range, and reductions in the consumption power and cost.

Another objective of the present invention is to provide an infrared moisture measuring method where high-speed response is possible and which is capable of accurately measuring the moisture value of mass produced lot products which flow intermittently.

The foregoing objectives are accomplished by providing an infrared moisture measuring apparatus which comprises a first infrared light-emitting diode (LED) for emitting infrared rays of a measuring beam whose infrared absorption varies by the moisture content of an object to be measured, a second infrared LED for emitting infrared rays of a reference beam whose infrared absorption does not substantially vary by the moisture content of an object to be measured, an optical system for illuminating the infrared rays of the measuring and reference beams emitted by the first and second infrared LEDs on the object to be measured and focusing the infrared rays reflected from the object to be measured through a lens, and an InGaAs light-receiving device for receiving the infrared rays focused by the optical system and outputting a light-received signal which corresponds to a light quantity of the received infrared rays. The moisture value of the object is obtained based on the light-received signal output from the InGaAs light-receiving device.

With this arrangement, the infrared rays of the measuring and reference beams are generated by the infrared LEDs, respectively. Also, the reflected beams of the measuring and reference beams from the object are received with the InGaAs light-receiving device, and the moisture value of the object is obtained based on the light-received signal output from the InGaAs light-receiving device. Accordingly, high-speed sampling, i.e., high-speed response is possible. In addition, compactness in the apparatus and enhancements in the maintenance and allowable operating environment temperature range can be achieved, and furthermore, reductions in the consumption power and cost can be achieved.

In the aforementioned infrared moisture measuring apparatus, temperature correction may be performed for the moisture value, based on an output of a temperature sensor provided near the first infrared LED. With this arrangement, accurate measurements can be performed.

In the aforementioned infrared moisture measuring apparatus, the optical system may be equipped with a half mirror by which the infrared rays emitted by one of the first and second LEDs are reflected and through which the infrared rays emitted by the other LED are transmitted, and the optical system may illuminate the reflected infrared rays and the transmitted infrared rays on the object with optical axes of the reflected and transmitted rays aligned with each other. With this arrangement, accurate measurements can be performed even in respect to a fluctuation in a distance of measurement.

In the aforementioned infrared moisture measuring apparatus, the optical system may also have a first reflecting surface which reflects the infrared rays for measurement and a second reflecting surface which reflects the infrared rays for reference, and the first and second reflecting surfaces may also be disposed in a positional relationship so that the infrared rays reflected by the first and second reflecting surfaces are illuminated on the object with an optical axis of the infrared rays reflected by the first reflecting surface aligned with that of the infrared rays reflected by the second reflecting surface. With this arrangement, the infrared rays emitted from the infrared LEDs can be illuminated nearly 100% on the object, so this embodiment is applicable to an object which has a low reflectance factor.

Also, there is provided an infrared moisture measuring apparatus which comprises a first infrared light-emitting diode (LED) for emitting infrared rays of a measuring beam whose infrared absorption varies by the moisture content of an object to be measured, a second infrared LED for emitting infrared rays of a reference beam whose infrared absorption does not substantially vary by the moisture content of an object to be measured, an optical system for illuminating the infrared rays of the measuring and reference beams emitted by the first and second infrared LEDs on the object to be measured and focusing the infrared rays reflected from the object to be measured through a lens, an InGaAs light-receiving device for receiving the infrared rays focused by the optical system and outputting a light-received signal which corresponds to a light quantity of the received infrared rays, and control means for measuring a moisture value of the object in correspondence with a detected state of the object by sampling the light-received signal output from the InGaAs light-receiving device at high speed when the object is being detected. With this arrangement, the moisture value of each one of products, such as mass produced lot products which flow intermittently, can be measured, and the average moisture value of mass produced lot products can be accurately measured.

In the aforementioned infrared moisture measuring apparatus, a first interference filter through which the infrared rays of the measuring beam are selectively transmitted may also be provided on a front face of the first infrared LED, and a second interference filter through which the infrared rays of the reference beam are selectively transmitted may also be provided on a front face of the second infrared LED.

In addition, there is provided an infrared moisture measuring method which illuminates a measuring beam emitted from a first infrared light-emitting diode (LED) and a reference beam emitted from a second infrared LED to an object to be measured, also receives reflected beams of the measuring and reference beams with an InGaAs light-receiving device through a lens, and furthermore obtains a moisture value of the object based on a light-received signal output from the InGaAs light-receiving device. The infrared moisture measuring method comprises the steps of (a) operating the first and second infrared LEDs at high speed, (b) detecting the object to be measured, (c) sampling the light-received signal of the InGaAs light-receiving device at high speed when the object is being detected, and (d) intermittently measuring the moisture value of the object in correspondence with a detected state of the object. Accordingly, the moisture value of each one of products, such as mass produced lot products which flow intermittently, can be measured, and the average moisture value of mass produced lot products can be accurately measured.

Furthermore, there is provided an infrared moisture measuring method which comprises the steps of (a) operating first and second infrared LEDs at high speed, (b) detecting an object to be measured, (c) sampling a light-received signal of an InGaAs light-receiving device at high speed when the object is being detected, (d) intermittently measuring the moisture value of the object in correspondence with a detected state of the object, and (e) sequentially displaying the measured moisture values when the object has been detected and holding and displaying the last one of the measured moisture values when the object is no longer detected. Accordingly, the moisture value of each one of products, such as mass produced lot products which flow intermittently, can be measured, and the average moisture value of mass produced lot products can be accurately measured. In addition, an instantaneous value can be known each time sampling is performed.

Furthermore, there is provided an infrared moisture measuring method which comprises the steps of (a) operating first and second infrared LEDs at high speed, (b) detecting an object to be measured, (c) sampling a light-received signal of an InGaAs light-receiving device at high speed when the object is being detected, (d) intermittently measuring the moisture value of the object in correspondence with a detected state of the object, and (e) holding and displaying an average moisture value of the moisture values, measured while the object is being detected, between the time that the object is no longer detected and the time that the next object is no longer detected and thereby updating and displaying the average moisture value of each object. Accordingly, the moisture value of each one of products, such as mass produced lot products which flow intermittently, can be measured, and the average moisture value of mass produced lot products can be accurately measured. In addition, an average moisture value can be known.

Moreover, there is provided an infrared moisture measuring method which comprises the steps of (a) operating first and second infrared LEDs at high speed, (b) detecting a moisture value of an object to be measured by sampling a light-received signal of an InGaAs light-receiving device at high speed, and (c) holding and displaying an average moisture value of the moisture values, measured when the measured moisture value is within a predetermined range, between the time that the measured moisture has gone out of the predetermined range and the time that the measured moisture has gone out of the predetermined range once again and thereby updating and displaying the average moisture value of each object. Accordingly, the moisture value of each one of products, such as mass produced lot products which flow intermittently, can be measured, and the average moisture value of mass produced lot products can be accurately measured. In addition, an average moisture value can be known.

Finally, there is provided an infrared moisture measuring method which comprises the steps of (a) operating first and second infrared LEDs at high speed, (b) detecting an object to be measured, (c) sampling a light-received signal of an InGaAs light-receiving device at high speed when the object is being detected, (d) intermittently measuring the moisture value of the object in correspondence with a detected state of the object, and (e) holding and displaying an average moisture value of the moisture values, measured when the object is detected and also a condition of the measured moisture value being within a predetermined range is satisfied, between the time that the condition is no longer satisfied and the time that the condition is no longer satisfied once again and thereby updating and displaying the average moisture value of each object. Accordingly, the moisture value of each one of products, such as mass produced lot products which flow intermittently, can be measured, and the average moisture value of mass produced lot products can be accurately measured. In addition, an average moisture value can be known.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be described in further detail with reference to the accompanying drawings, in which.

DETAILED DESCRIPTION OF THE PREFERRED EMBODIMENTS

Figure 1:
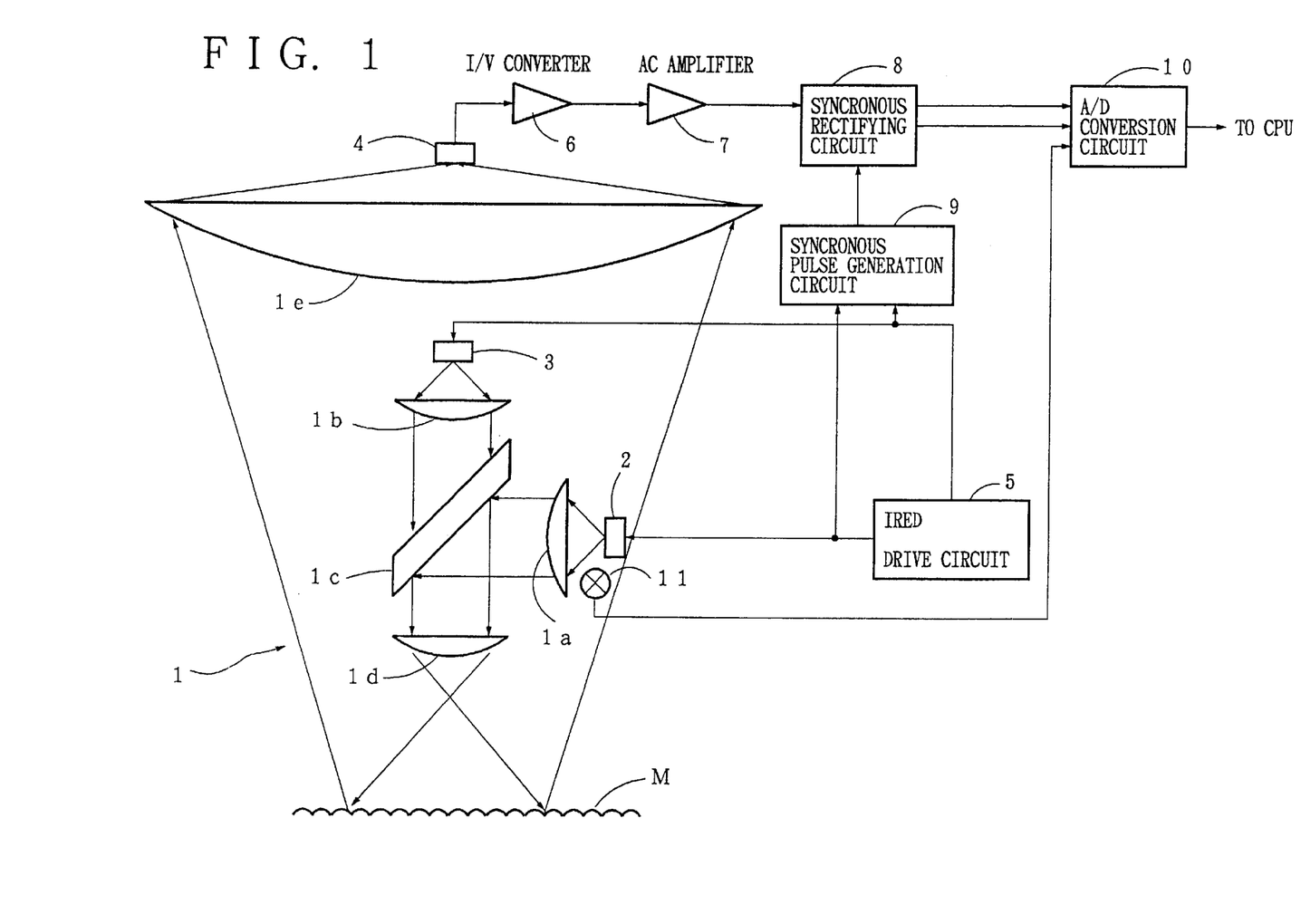
FIG. 1 is a block diagram showing an infrared moisture measuring apparatus which is a first embodiment of the present invention.

Referring now in greater detail to the drawings and initially to FIG. 1, there is shown an infrared moisture measuring apparatus constructed in accordance with a first embodiment of the present invention. The optical system 1 of the infrared moisture measuring apparatus is equipped with a measuring-beam collecting lens 1a, a reference-beam collecting lens 1b, a half mirror 1c, an illuminating-beam collecting lens 1d, and a reflected-beam collecting lens 1e. The optical axis of the reference-beam collecting lens 1b is aligned with that of the illuminating-beam collecting lens 1d. The half mirror 1c is disposed at an angle of 45° to the optical axis of the illuminating-beam collecting lens 1d.

The measuring-beam collecting lens 1a is disposed so that its axis orthogonally crosses that of the reference-beam collecting lens 1b at the reflecting surface of the half mirror 1c. Behind the measuring-beam collecting lens 1a there is disposed a measuring-beam IRED (infrared light-emitting diode) 2 which outputs near-infrared rays with a dominant wavelength of 1.45 $\mu$m, i.e., near-infrared rays whose infrared absorption is varied by the moisture content of an object to be measured, as a measuring beam. Behind the reference-beam collecting lens 1b there is disposed a reference-beam LED 3 which outputs near-infrared rays with a dominant wavelength of 1.3 $\mu$m, i.e., near-infrared rays whose infrared absorption is not varied by the moisture content of an object to be measured, as a reference beam. Furthermore, an InGaAs (indium-gallium-arsenic) detector 4 is disposed at the beam focused point of the reflected-beam collecting lens 1e.

The measuring-beam IRED 2 and the reference-beam IRED 3 are driven by time division with an IRED drive circuit 5 so that a measuring beam and a reference beam are alternately emitted. The measuring beam emitted from the measuring-beam IRED 2 is collimated by the measuring-beam collecting lens 1a. The collimated beam is orthogonally reflected 50% by the half mirror 1c. The reflected beam is illuminated on the surface M of an object to be measured with the illuminating-beam collecting lens 1d. On the other hand, the reference beam emitted from the reference-beam IRED 3 is collimated by the reference-beam collecting lens 1b. 50% of the collimated beam is transmitted through the half mirror 1c. The transmitted beam is illuminated on the surface M of the object with the illuminating-beam collecting lens 1d. The measuring beam reflected by the half mirror 1c and the reference beam transmitted through the half mirror 1c are illuminated on the object with the respective optical axes of the beams aligned with each other.

The measuring beam and the reference beam reflected at the surface M of the object are focused on the InGaAs detector 4 by the reflected-beam collecting lens 1e. At this InGaAs detector 4, currents with levels corresponding to the intensities of the light quantities of the measuring beam and the reference beam are alternately output as a light-received signal. The light-received signal output from the InGaAs detector 4 is converted to a voltage signal by an I/V converter 6. Then, the voltage signal is amplified by an AC amplifier 7 and is input to a synchronous rectifying circuit 8.

The drive signals, output from the IRED drive circuit 5 to drive the measuring-beam IRED 2 and the reference-beam IRED 3, are input to a synchronous pulse generation circuit 9. The synchronous pulse generation circuit 9 generates a pulsed signal synchronized with the input drive signal and outputs it to the synchronous rectifying circuit 8.

The synchronous rectifying circuit 8 rectifies the voltage signal output from the AC amplifier 7 and also separates this rectified DC signal into the voltage signal of the measuring beam and the voltage signal of the reference beam in synchronization with the pulsed signal from the synchronous pulse generation circuit 9. The voltage signals are output from the output terminals provided in correspondence with the measuring beam and the reference beam to an A/D conversion circuit 10. Then, the A/D conversion circuit converts the analog voltage signals to digital signals (numerical data) which correspond to the measuring beam and the reference beam, respectively, and the converted digital signals are output to a central processing unit (CPU) (not shown).

Here, in the object to be measured, absorption of the measuring beam occurs in correspondence with the moisture content and the other main causes and also absorption of the reference beam occurs in correspondence with the aforementioned other main causes. Therefore, by a ratio of the measuring beam to the beam quantity of the reflected beam and a ratio of the reference beam to the beam quantity of the reflected beam, or the logarithms, a converted absorbance value eliminating the influence of the aforementioned other main causes can be obtained. This converted absorbance value can be converted to a moisture value by an equation of a previously set measuring line, etc.

Based on the digital signal from the A/D conversion circuit 10, the aforementioned CPU calculates a converted absorbance value and a moisture value and outputs the results as the measured values. In this embodiment shown in FIG. 1, a temperature sensor 11 is provided near the measuring-beam IRED 2, a voltage signal corresponding to the output voltage of this temperature sensor 11, i.e., a voltage signal corresponding to temperature is converted to a digital signal by the A/D conversion circuit 10, and based on the digital signal corresponding to temperature, the CPU performs temperature correction.

According to the aforementioned embodiment shown in FIG. 1, a measuring beam is reflected at the half mirror 1c and a reference beam is transmitted trough the half mirror 1c. Also, the respective axes of the beams are aligned with each other. Therefore, the optical system becomes compact. In addition, since a measuring beam and a reference beam are illuminated on an object to be measured with the respective axes aligned with each other, accurate measurements can be performed even in respect to a fluctuation in the distance from the optical system to the object to be measured, i.e., distance of measurement.

Figure 2:
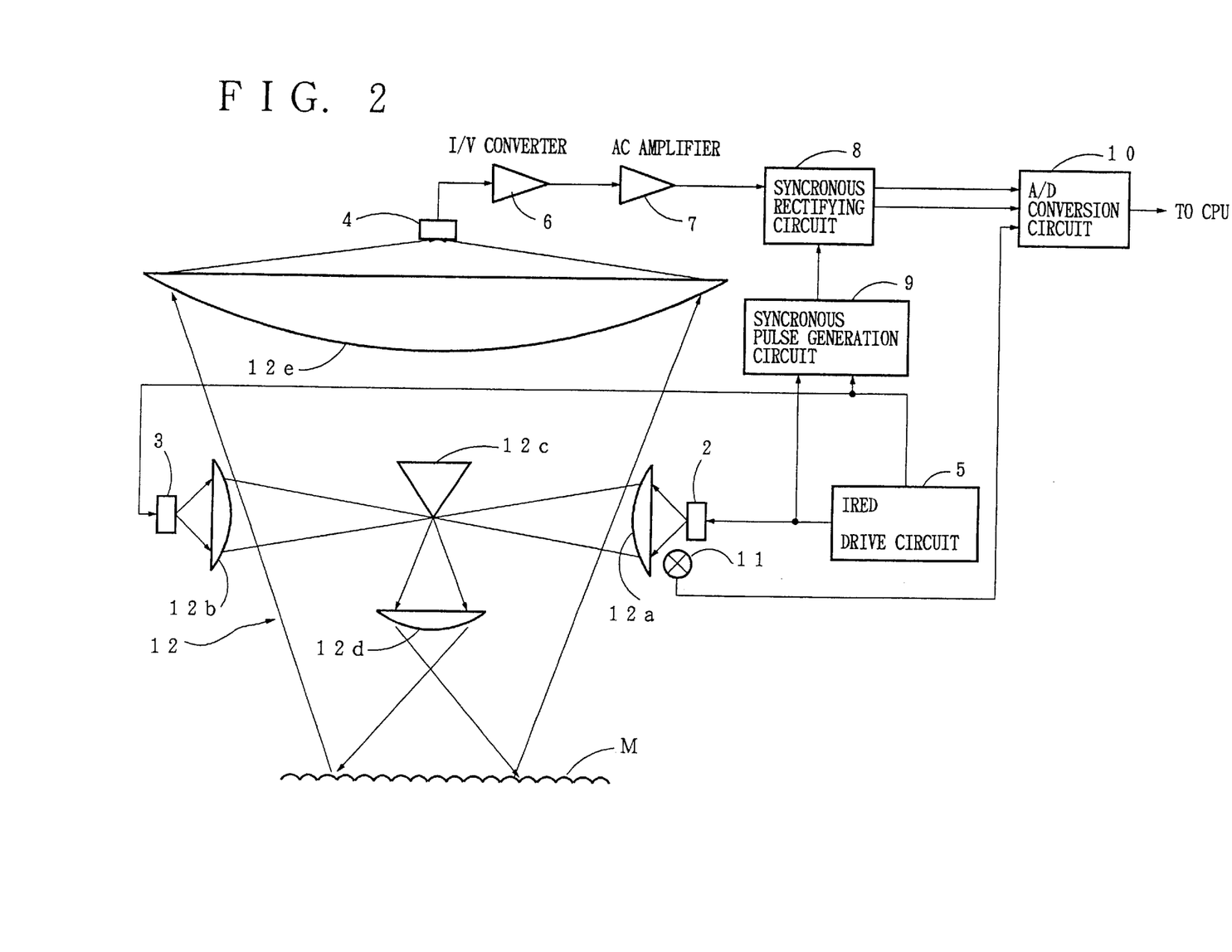
FIG. 2 is a block diagram showing an infrared moisture measuring apparatus which is a second embodiment of the present invention.

Referring to FIG. 2, there is shown an infrared moisture measuring apparatus constructed in accordance with a second embodiment of the present invention. The differing points of the apparatus of FIG. 2 from that of FIG. 1 are only the structure of an optical system 12 and the positional relation between a measuring-beam IRED 2 and a reference-beam IRED 3, and the circuit operation is the same as that of the apparatus shown in FIG. 1. The same reference numerals are applied to the same parts as FIG. 1 and therefore a detailed description is omitted for avoiding redundancy.

The optical system 12 is constituted by a measuring-beam collecting lens 12a, a reference-beam collecting lens 12b, a prism 12c, an illuminating-beam lens 12d, and a reflected-beam collecting lens 12e. The vertical angle θ of the prism 12c is 90°, and the positional relation between the prism 12c and the illuminating-beam collecting lens 12d is set so that the optical axis of the illuminating-beam collecting lens 12d divides the vertical angle θ into two equal parts.

The measuring-beam collecting lens 12a and the reference-beam collecting lens 12b are disposed symmetrically with respect to the optical axis of the illuminating-beam collecting lens 12d. Behind the measuring-beam collecting lens 12a there is disposed the measuring-beam IRED 2 which outputs near-infrared rays of dominant wavelength 1.45 μm as a measuring beam. Behind the reference-beam collecting lens 12b there is disposed the reference-beam IRED 3 which outputs near-infrared rays of dominant wavelength 1.3 μm as a reference beam.

The measuring-beam collecting lens 12a and the reference-beam collecting lens 12b are respectively set so that the respective optical axes pass through the reflecting surfaces forming the vertical angle θ of the prism 12c and orthogonally cross the optical axis of the illuminating-beam collecting lens 12d in the vicinity of the ridge line into which the reflecting surfaces of the prism 12c merge. The focal lengths and positions of the measuring-beam collecting lens 12a and the reference-beam collecting lens 12b are set so that the measuring beam from the measuring-beam IRED 2 and the reference beam from the reference-beam IRED 3 are focused to points on the reflecting surfaces of the prism 12c, respectively.

With the aforementioned arrangement, the measuring beam focused to a point by the measuring-beam collecting lens 12a and the reference beam focused to a point by the reference-beam collecting lens 12b are orthogonally reflected with a reflectance factor of 100% at the reflecting surfaces of the prism 12c, respectively. The reflected beams are illuminated on the surface M of an object to be measured along the optical axis of the illuminating-beam collecting lens 12d. Based on the reflected beams from this reflecting surface M, a moisture value is measured in the same way as described above.

In the infrared moisture measuring apparatus of the aforementioned first embodiment shown in FIG. 1, the measuring beam emitted from the measuring-beam IRED 2 is reflected by the half mirror 1c and the reference beam emitted from the reference-beam IRED 3 is transmitted through the half mirror 1c, so 50% of each beam of infrared rays is lost. However, in the infrared moisture measuring apparatus of the aforementioned second embodiment of FIG. 2, the measuring beam and the reference beam are reflected 100% by the prism 12c, so infrared rays can be effectively utilized and this apparatus is also applicable to an object which has a low reflectance factor.

Figure 3:
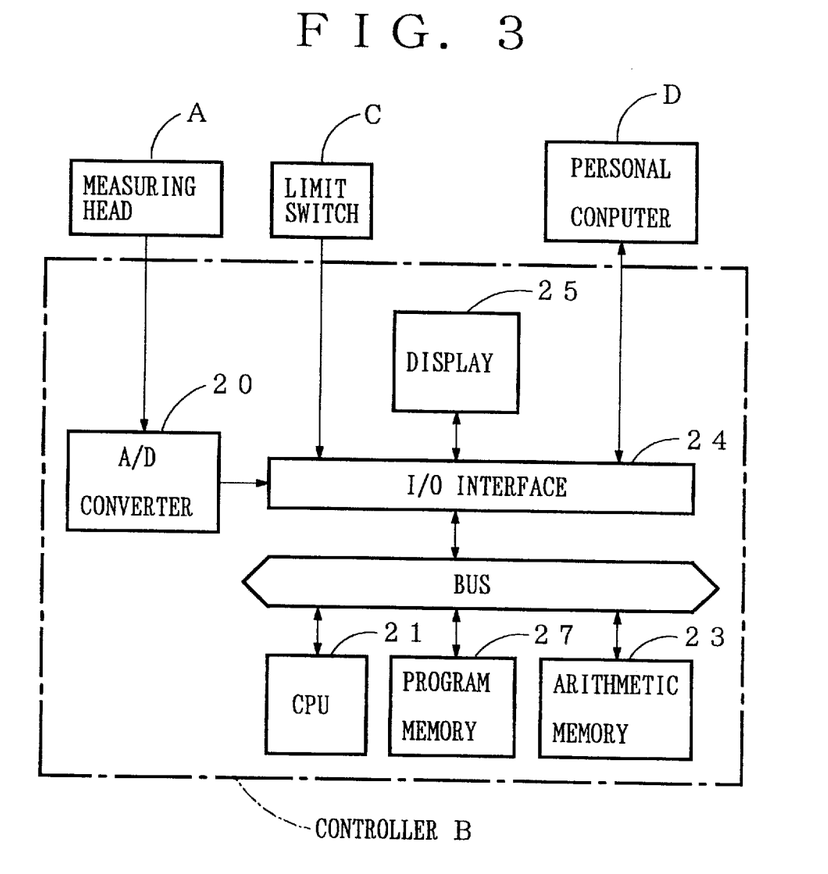
FIG. 3 is a block diagram showing an infrared moisture measuring apparatus which is a third embodiment of the present invention.
Figure 4:
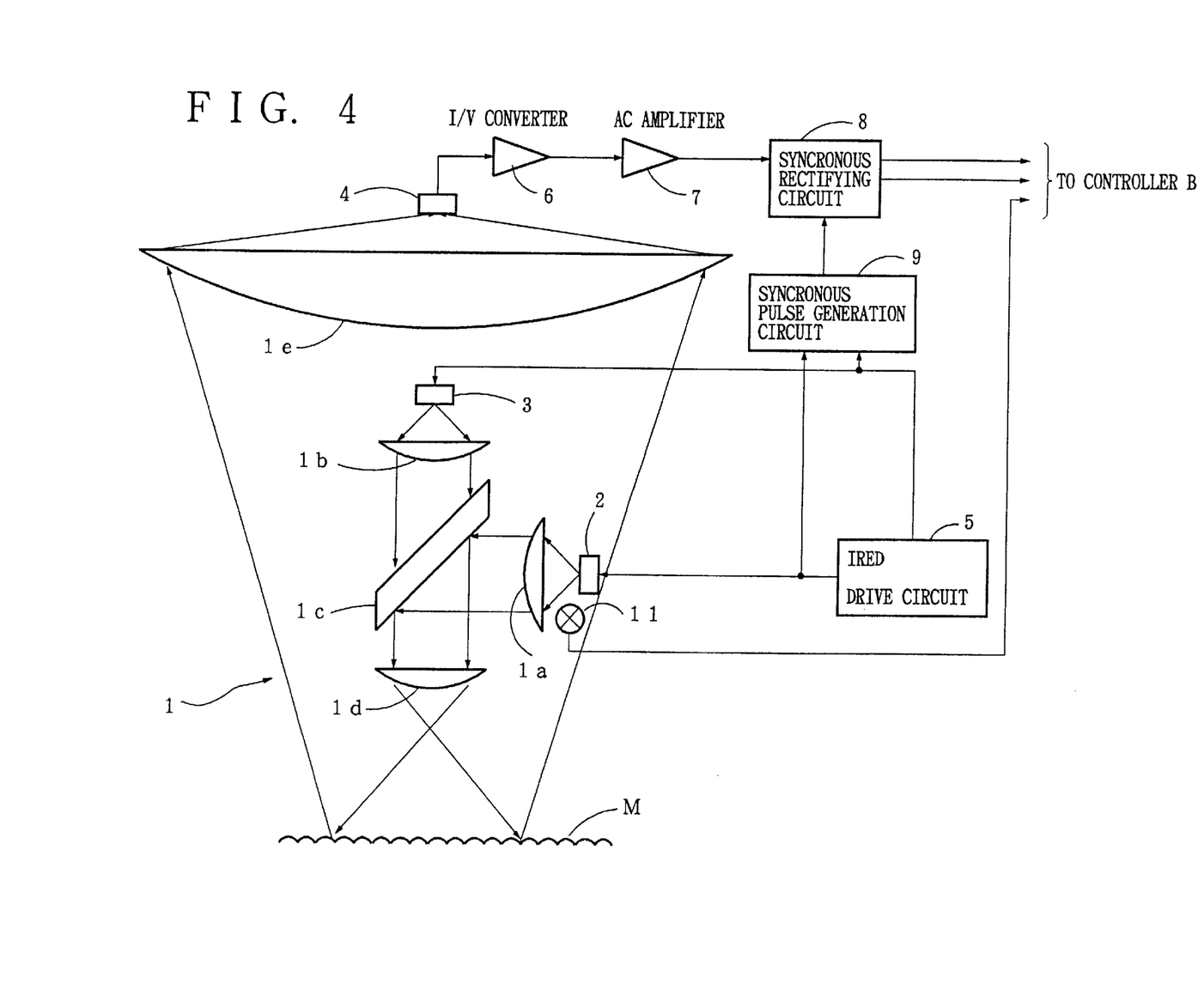
FIG. 4 is a block diagram showing the measuring head of the infrared moisture measuring apparatus shown in FIG. 3.

FIG. 3 schematically shows an infrared moisture measuring apparatus of a third embodiment of the present invention, and FIG. 4 schematically shows the measuring head A of the infrared moisture measuring apparatus shown in FIG. 3. As shown in the figure, the infrared moisture measuring apparatus of this embodiment is roughly constituted by the measuring head A and controller B. Connected to the controller B is a photoelectric limit switch C which detects the existence of a product on a conveyor which is an object to be measured. Also connected to the controller B is a personal computer D. The personal computer D generates data for a measuring line which corresponds to an object to be measured. The generated data for a measuring line and the data for a measuring line previously obtained according to an object to be measured are set to the controller B.

The controller B is constituted by a microcomputer equipped with an A/D converter 20. Based on a control program stored on a program memory 22, a CPU 21 performs various arithmetic processing, using an arithmetic memory 23. Also, through an I/O interface 24, data is input and output between the A/D converter 20, a display 25, and the personal computer D. Furthermore, an ON/OFF signal from the limit switch C is input to the I/O interface 24 as an external hold signal.

As shown in FIG. 4, the measuring head A, as with the first embodiment of FIG. 1, is constituted by an optical system 1, a measuring-beam IRED 2, a reference-beam IRED 3, an InGaAs detector 4, an IRED drive circuit 5, an I/V converter 6, an AC amplifier 7, a synchronous rectifying circuit 8, and a synchronous pulse generation circuit 9. The parts with the same reference numerals as FIG. 1 are identical in construction with those of the first embodiment and therefore a detailed description is omitted for avoiding redundancy. Note that the voltage signals of the measuring beam and reference beam from the synchronous rectifying circuit 8 are input to the A/D converter 20 of the controller B shown in FIG. 3.

In FIG. 3 the A/D converter 20 converts an analog voltage signal to a digital signal (numerical data), and this digital signal is transferred to the CPU 21 through the I/O interface 24. Then, the CPU 21 calculates absorbance, based on the measuring beam data S corresponding to a measuring beam and the reference beam data R corresponding to a reference beam. From this calculated absorbance and the previously set data of a measuring line, a moisture value is calculated and displayed on the display 25. In this embodiment shown in FIG. 3, there are cases where, according to measuring modes to be described later, the average moisture value of calculated moisture values of each object is displayed on the display 25. Also, in this embodiment a temperature sensor 11 is provided near the measuring-beam IRED 2. The output voltage of the temperature sensor 11, that is, a voltage signal corresponding to temperature is converted to a digital signal with the A/D converter 20, and based on the digital signal corresponding to temperature, the CPU 21 makes a temperature correction.

The infrared moisture measuring apparatus of the embodiment shown in FIGS. 3 and 4 has four kinds of measuring modes, mode 0 through mode 3. These measuring modes are specified by the personal computer D or the controller B. Also, in this embodiment, an object to be measured is detected when the external hold signal from the limit switch C is in its OFF state, and when the apparatus is in modes 1 through 3, a moisture value is intermittently measured based on the external hold signal.

For example, when objects to be measured are spaced and conveyed on a conveyor, the limit switch C is constituted by emitting a beam so as to cross a conveying path for these objects and receiving this beam with a photoelectric detector. If the object blocks the beam, the limit switch C will be turned off, and if the object passes through the beam, the limit switch C will be turned on. Therefore, the moisture value of an object to be measured is measured when the limit switch C is in its OFF state. Note that, in the case of mode 0, each time the measuring beam data S and the reference beam data R are sampled, a moisture value is calculated at all times regardless of the external hold signal output from the limit switch C and the calculated moisture value is displayed on the display 25.

Now, based on timing diagrams of FIGS. 5 through 8, a description will be made of modes 1 through 3. In each timing diagram, the shaded blocks represent, for example, objects which intermittently flow on a conveyor. The external hold signal (a), output from the limit switch C, goes to the ON state when an object to be measured is not present and goes to the OFF state when an object to be measured is present.

Figure 5:
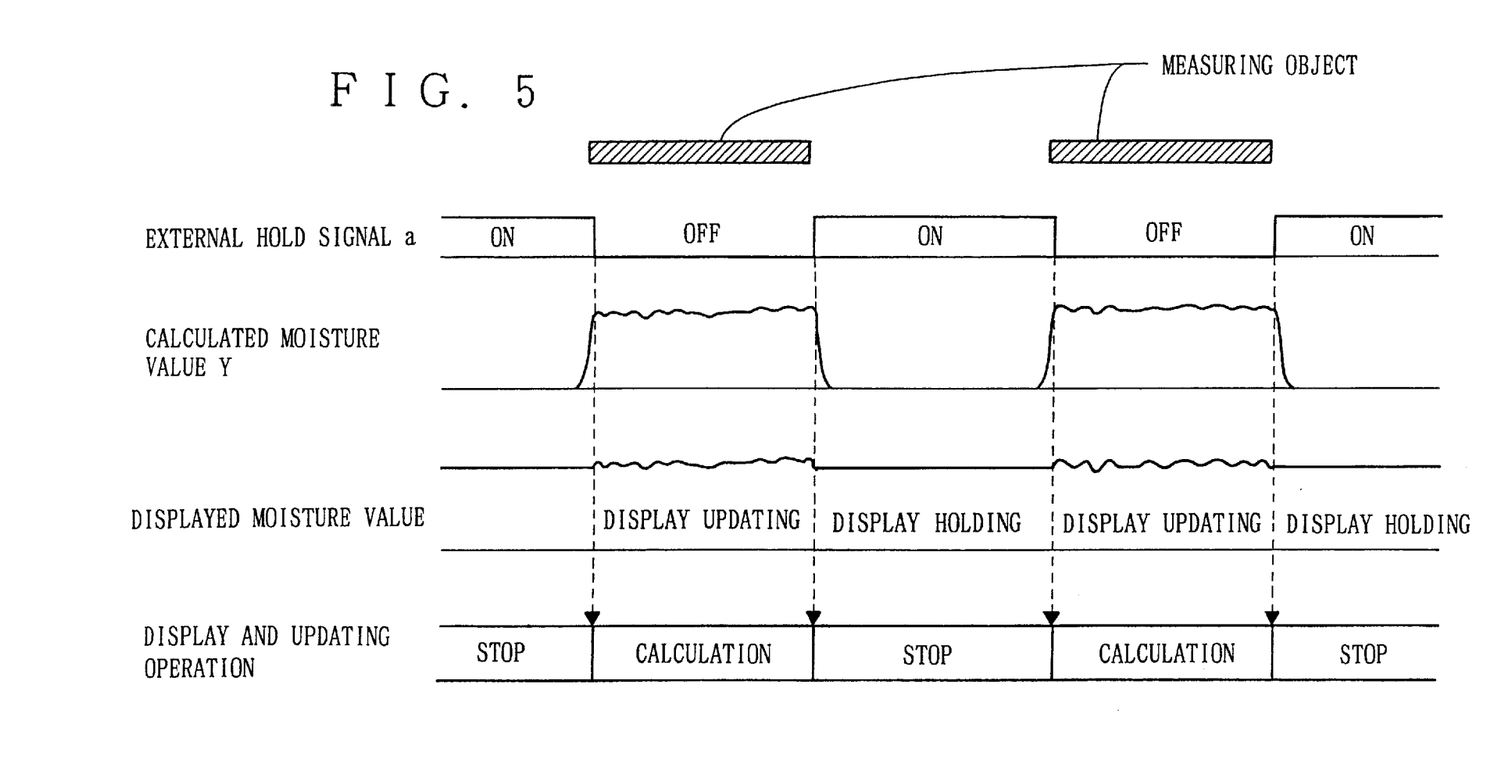
FIG. 5 is a timing diagram showing mode 1 of the third embodiment.

FIG. 5 shows the case of mode 1. In mode 1, when the external hold signal (a) is in the OFF state, a calculated moisture value Y is obtained and sequentially updated with the measuring beam data S and the reference beam data R which are sequentially obtained. The updated value, as it is, is displayed on the display 25. If, on the other hand, the external hold signal (a) goes to the ON state, the immediately prior calculated moisture value Y is held and displayed on the display 25 until the external hold signal (a) goes to the OFF state once again.

Figure 6:
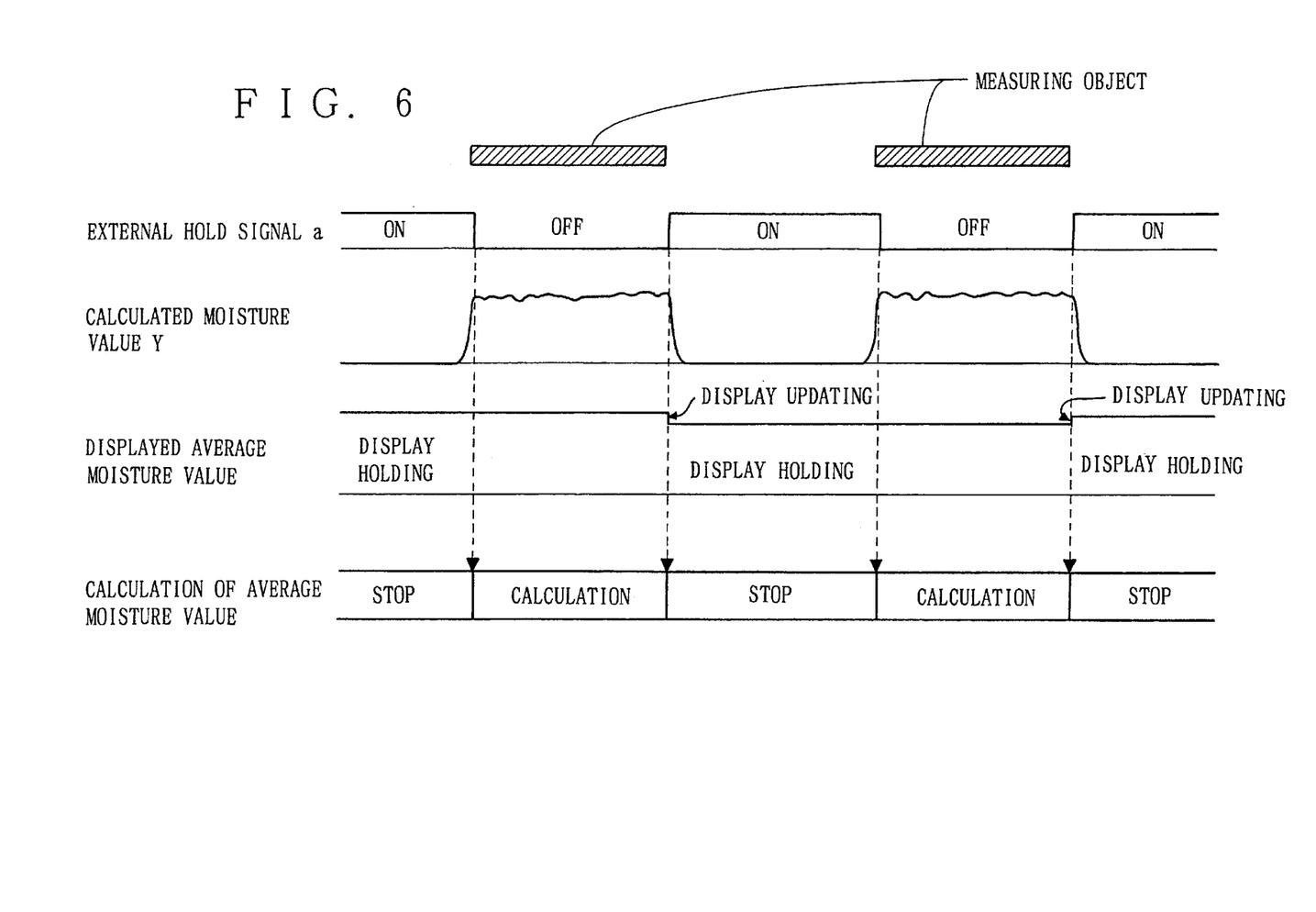
FIG. 6 is a timing diagram showing mode 2 of the third embodiment.

FIG. 6 shows the case of mode 2. In mode 2, when the external hold signal (a) is in the OFF state, a calculated moisture value Y is obtained with the measuring beam data S and the reference beam data R which are sequentially obtained, and also an average moisture value is calculated. The average moisture value during the OFF state of the external hold signal is displayed on the display 25 at the time the external hold signal has gone to the ON state. That is, during the time the external hold signal (a) is in the OFF state, the average moisture value of an object of immediately prior one before is held and displayed, and if the external hold signal (a) goes to the ON state, that is, if an object to be measured is no longer detected, the average moisture value of the object will be held and displayed. Thus, the average moisture value of each object is displayed until the time the measurement of the next object has ended.

Figure 7:
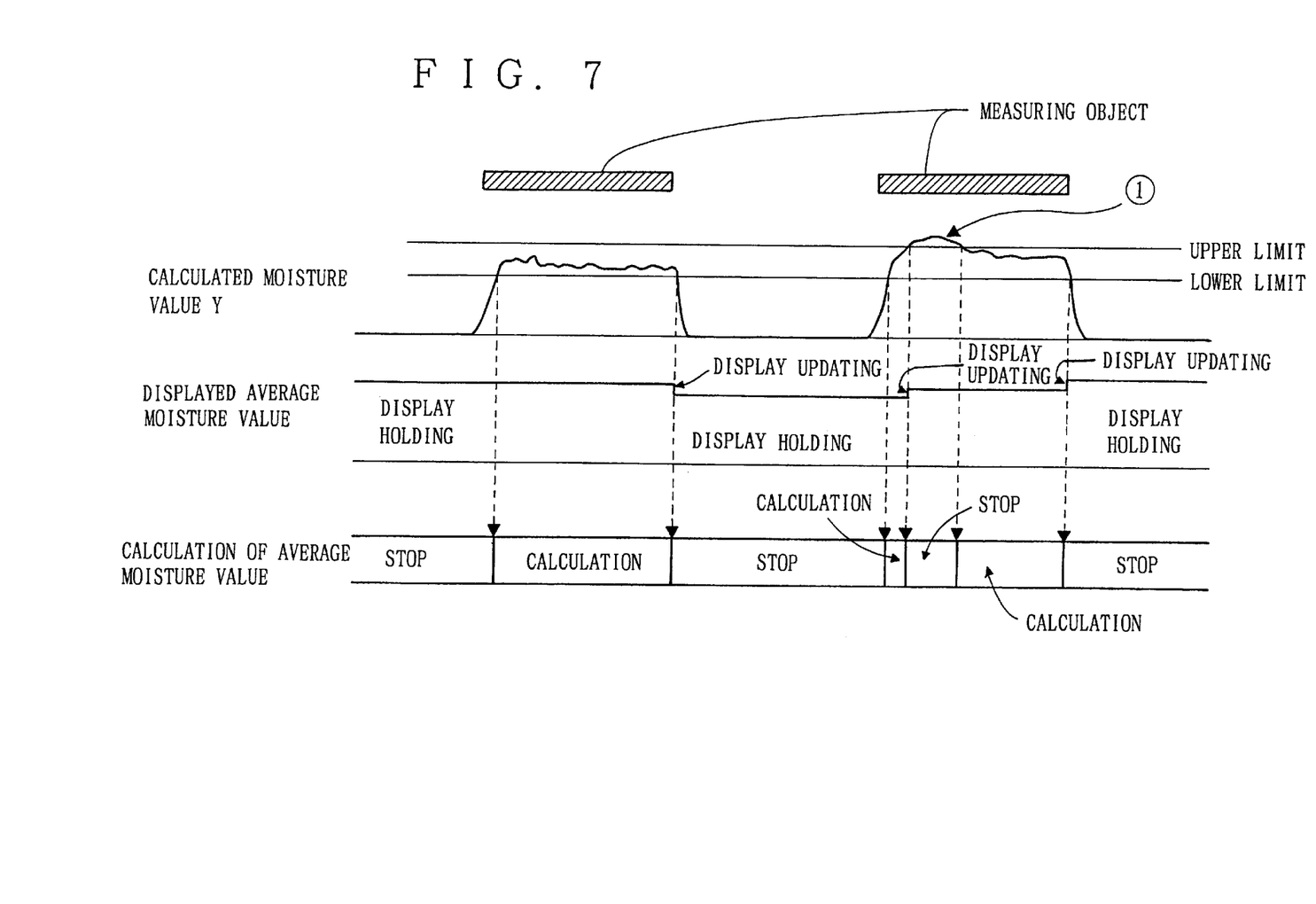
FIG. 7 is a timing diagram showing the case where a limit switch is not connected in mode 3 of the third embodiment.

FIG. 7 shows the case where the limit switch C is not connected in mode 3. In mode 3, switching of calculation and display are controlled according to a predetermined threshold value relative to the calculated moisture value Y. That is, the threshold value has an upper limit value and a lower limit value. Only when the calculated moisture value Y is between the upper limit value and the lower limit value (lower limit value≦calculated moisture value Y≦upper limit value), the average moisture value of the calculated moisture values Y is calculated. The average moisture value when the calculated moisture value Y is between the upper limit value and the lower limit is displayed on the display 25 at the time the calculated moisture value Y has gone out of the upper limit value or the lower limit value. Also, when the calculated moisture value Y goes out of the upper limit value or the lower limit value, the calculation of the average moisture value is stopped. Thus, for example, when a moisture value is abnormal as shown by (1) in FIG. 7 (an abnormally high value for this case), the abnormal moisture value can be made so as not to have an influence on an average moisture value. Even in the case of this mode 3, as with the case of mode 2, the average moisture value of each object is displayed until the time the measurement of the next object ends.

Figure 8:
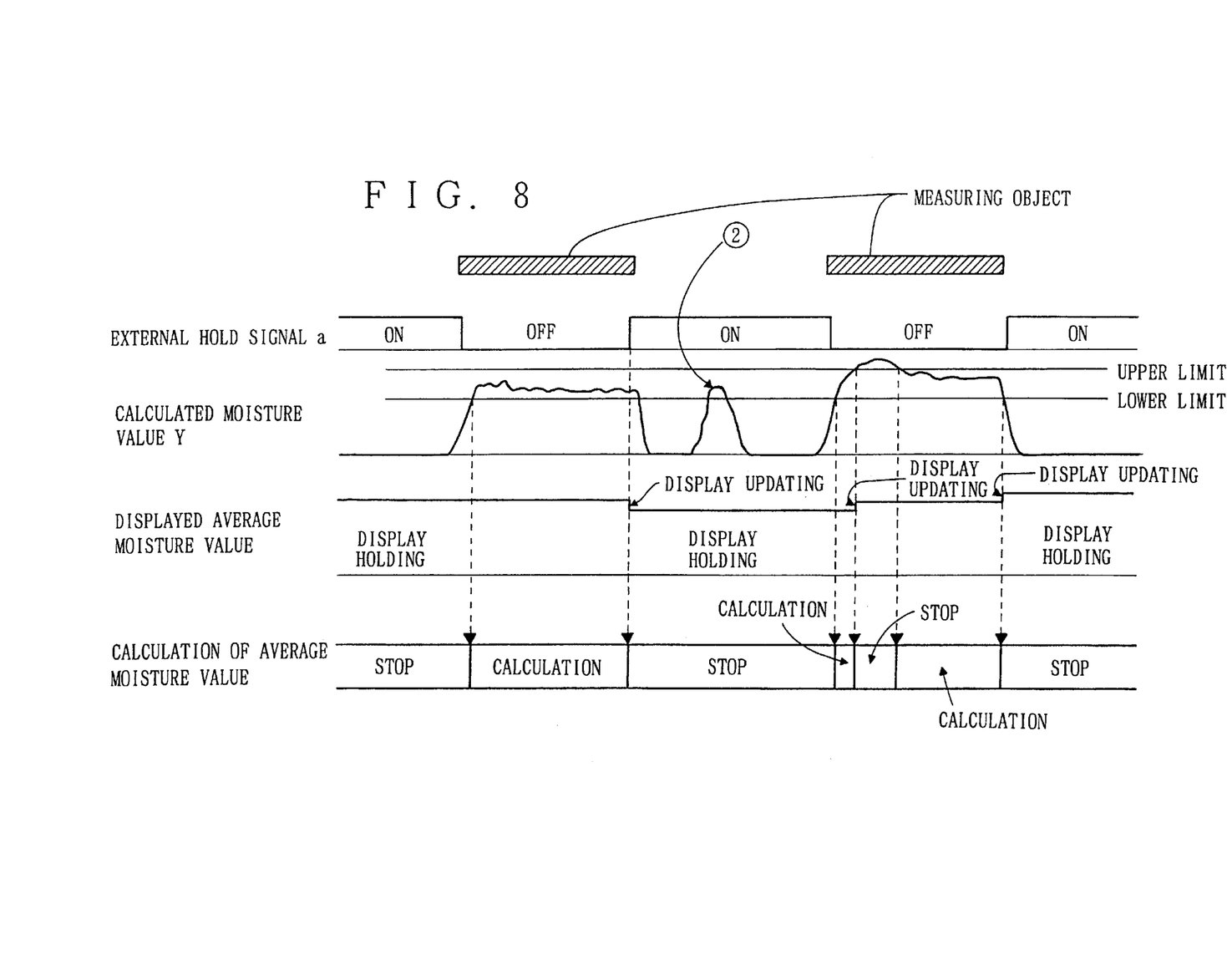
FIG. 8 is a timing diagram showing the case where the limit switch is connected in mode 3 of the third embodiment.

FIG. 8 shows the case where the limit switch C is connected in mode 3. In mode 3, switching of calculation and display are controlled according to the state of the external hold signal (a) and, as with the aforementioned case, the predetermined threshold value relative to the calculated moisture value Y. Only when the external hold signal (a) is in the OFF state and the calculated moisture value Y is between the upper limit value and the lower limit value (lower limit value≦calculated moisture value Y≦upper limit value), the average moisture value of the calculated moisture values Y is calculated. The average moisture value, during this OFF period and also when the calculated moisture value Y is between the upper limit value and the lower limit, is displayed on the display 25 at the time the external hold signal has gone to the ON state or at the time the calculated moisture value Y has gone out of the upper limit value or the lower limit value. Also, at conditions other than this, the calculation of the average moisture value is stopped. Thus, as with the aforementioned case, when a moisture value is abnormal, the value can be made so as not to have an influence on an average moisture value. Furthermore, for example, even in the case where a certain degree of calculated moisture value occurred due to a foreign substance such as having no influence on the external hold signal (a) as shown by (2) in FIG. 8, the value can be made so as not to have an influence on an average moisture value. Even in the case of this mode 3, as with the case of mode 2, the average moisture value of each object is displayed until the time the measurement of the next object ends.

In the moisture measurement described above, (1) the calculated moisture value Y and the calculated average moisture value when the external hold signal (a) is in the OFF state in modes 1 and 2, or (2) in the case where the limit switch C is not connected in mode 3, the calculated average moisture value when a condition of (lower limit value≦calculated moisture value Y≦upper limit value) is satisfied, or (3) in the case where the limit switch C is connected in mode 3, the calculated average moisture value when the external hold signal (a) is in the OFF state and also when a condition of (lower limit value≦calculated moisture value Y≦upper limit value) is satisfied, is transferred, for example, to the personal computer D, and based on these calculated moisture values, an average moisture value of the whole of a plurality of objects can be obtained. Thus, moisture values are intermittently measured in synchronization with objects to be measured. Therefore, for a great number of objects of the same kind, for example, mass produced lot products, the average moisture value can be accurately measured.

From the fact that, in mode 3, when the calculated moisture value Y is between the upper and lower limit values, it is judged that an object to be measured is present, the rough moisture values of an object to be measured are usually known, so the threshold value can be set from these known moisture values.

While moisture measurement is performed as described above, the responsiveness of the measuring-beam IRED 2, reference-beam IRED 3, and InGaAs detector 4 of the measuring head A are high and, for example, they can be started up in about 0.2 sec after start of measurement. Furthermore, the sampling cycles of the measuring beam data S and the reference beam data R can be extremely shortened. Therefore, for example, during the time the external signal (a) is in the OFF state (for example, during about 1 sec or less), calculated moisture values can be sampled at a great number of points, so an accurate representative moisture value of each of the objects can be obtained.

In the aforementioned embodiments, while the infrared rays of the measuring and reference beams have been emitted by the measuring-beam IRED 2 and the reference-beam IRED 3, these IREDs and filters respectively corresponding to the wavelengths of the IREDs can be used together to make the measuring beam and the reference beam monochromatic.

Figure 9:
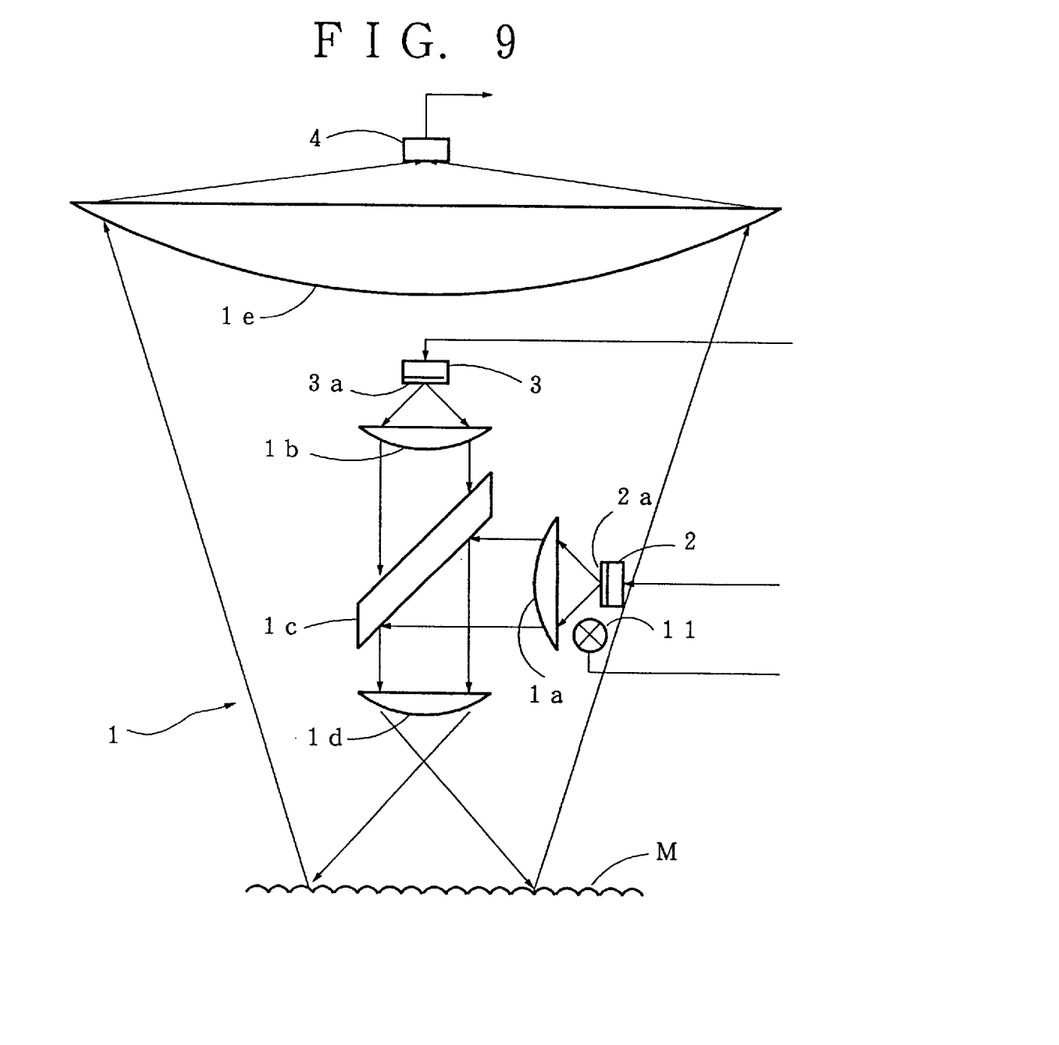
FIG. 9 is a diagram showing an example of an optical system where filters are applied to the first and third embodiments.
Figure 10:
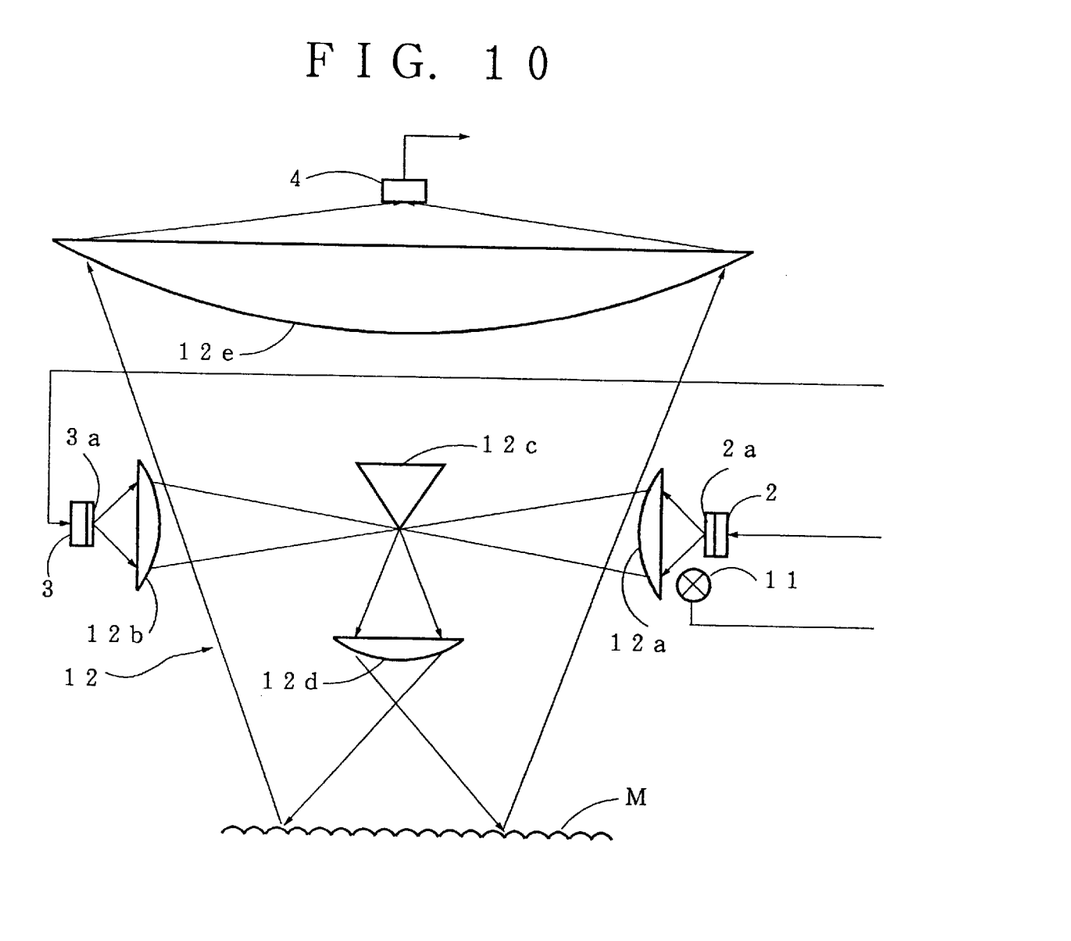
FIG. 10 is a diagram showing an example of an optical system where filters are applied to the second embodiment.

FIG. 9 schematically shows an example of an optical system where filters are applied to the first and third embodiments, and FIG. 10 schematically shows an example of an optical system where filters are applied to the second embodiment. In the figures, a measuring-beam interference filter 2a is disposed on the front face of each measuring-beam IRED 2 so that the infrared rays in a narrow wavelength band, including a dominant wavelength of 1.45 μm, are selectively transmitted through, and a reference-beam interference filter 3a is disposed on the front face of each measuring-beam IRED 3 so that the infrared rays in a narrow wavelength band, including a dominant wavelength of 1.3 μm, are selectively transmitted through.

The aforementioned embodiments of FIGS. 9 and 10 do not require a structure where a filter wheel is rotated with a motor, as prior art does. Therefore, the apparatus itself becomes compact, the number of essential parts can be decreased, and the cost can be reduced.

In addition, since the measuring-beam IRED 2 and the reference-beam IRED 3 are constituted by infrared light-emitting diodes, they have a long lifetime and less consumption current and do not become a heat generating body, and furthermore, enhancements in the maintenance and allowable operating environment temperature range and a reduction in the consumption power can be achieved. In addition, since the measuring-beam IRED 2 and the reference-beam IRED 3 can be operated at high speed, high-speed sampling, i.e., high-speed response becomes possible, and the moisture measurement of samples, such as confectionery products or tablets, which are particularly small and flow intermittently on a conveyor, becomes possible.

Furthermore, the InGaAs detector 4 is 10 times higher in sensitivity than a PbS detector, and yet, the device characteristics are stable and the responsiveness is excellent. Moreover, the peak of the spectral sensitivity of the InGaAs detector 4 is at 1.55 μm and the detection sensitivity is higher than that of a PbS detector by one figure. Because infrared rays with a dominant wavelength of 1.45 μm have been employed as a measuring beam, sufficient measurement becomes possible for a wide range from a low moisture sample up to a high moisture sample.

While the invention has been described with reference to preferred embodiments thereof, the invention is not to be limited to the details given herein, but may be modified within the scope of the appended claims.

What is claimed is:

1. An infrared moisture measuring apparatus comprising:

a first infrared light-emitting diode (LED) for emitting infrared rays of a measuring beam whose infrared absorption varies by the moisture content of an object to be measured;

a second infrared LED for emitting infrared rays of a reference beam whose infrared absorption does not substantially vary by the moisture content of an object to be measured;

an optical system for illuminating the infrared rays of the measuring and reference beams emitted by said first and second infrared LEDs on the object, the optical system including a lens for focusing the infrared rays reflected from said object;

an InGaAs light-receiving device for receiving the infrared rays focused by said optical system and outputting a light-received signal which corresponds to a light quantity of the received infrared rays; and a processing system for obtaining a moisture value of the object based on the light-received signal output from said InGaAs light-receiving device, wherein said optical system is equipped with a half mirror by which the infrared rays emitted by one of the first and second LEDs are reflected and through which the infrared rays emitted by the other LED are transmitted, and wherein said optical system illuminates the reflected infrared rays and the transmitted infrared rays on said object with optical axes of the reflected and transmitted rays aligned with each other.

2. The infrared moisture measuring apparatus as set forth in claim 1, further comprising a temperature sensor provided near said first infrared LED for outputting a temperature signal to be utilized in performing a temperature correction for said moisture value.

3. An infrared moisture measuring apparatus comprising:

a first infrared light-emitting diode (LED) for emitting infrared rays of a measuring beam whose infrared absorption varies by the moisture content of an object to be measured;

a second infrared LED for emitting infrared rays of a reference beam whose infrared absorption does not substantially vary by the moisture content of an object to be measured;

an optical system for illuminating the infrared rays of the measuring and reference beams emitted by said first and second infrared LEDs on the object, the optical system including a lens for focusing the infrared rays reflected from said object;

an InGaAs light-receiving device for receiving the infrared rays focused by said optical system and outputting a light-received signal which corresponds to a light quantity of the received infrared rays; and a processing system for obtaining a moisture value of the object based on the light-received signal output from said InGaAs light-receiving device, wherein said optical system has a first reflecting surface which reflects the infrared rays for measurement and a second reflecting surface which reflects the infrared rays for reference, and wherein said first and second reflecting surfaces are disposed in a positional relationship so that the infrared rays reflected by said first and second reflecting surfaces are illuminated on said object with an optical axis of the infrared rays reflected by said first reflecting surface aligned with that of the infrared rays reflected by said second reflecting surface.

4. The infrared moisture measuring apparatus as set forth in claim 3, wherein said first and second reflecting surfaces are surfaces of a prism.

5. An infrared moisture measuring apparatus comprising:

a first infrared light-emitting diode (LED) for emitting infrared rays of a measuring beam whose infrared absorption varies by the moisture content of an object to be measured;

a second infrared LED for emitting infrared rays of a reference beam whose infrared absorption does not substantially vary by the moisture content of an object to be measured;

an optical system for illuminating the infrared rays of the measuring and reference beams emitted by said first and second infrared LEDs on the object, the optical system including a lens for focusing the infrared rays reflected from said object;

an InGaAs light-receiving device for receiving the infrared rays focused by said optical system and outputting a light-received signal which corresponds to a light quantity of the received infrared rays; and control means for measuring a moisture value of the object in correspondence with a detected state of the object by sampling the light-received signal output from said InGaAs light-receiving device at high speed when said object is being detected, wherein said optical system is equipped with a half mirror by which the infrared rays emitted by one of the first and second LEDs are reflected and through which the infrared rays emitted by the other LED are transmitted, and wherein said optical system illuminates the reflected infrared rays and the transmitted infrared rays on said object with optical axes of the reflected and transmitted rays aligned with each other.

6. An infrared moisture measuring apparatus comprising:

a first infrared light-emitting diode (LED) for emitting infrared rays of a measuring beam whose infrared absorption varies by the moisture content of an object to be measured;

a second infrared LED for emitting infrared rays of a reference beam whose infrared absorption does not substantially vary by the moisture content of an object to be measured;

an optical system for illuminating the infrared rays of the measuring and reference beams emitted by said first and second infrared LEDs on the object, the optical system including a lens for focusing the infrared rays reflected from said object;

an InGaAs light-receiving device for receiving the infrared rays focused by said optical system and outputting a light-received signal which corresponds to a light quantity of the received infrared rays; and control means for measuring a moisture value of the object in correspondence with a detected state of the object by sampling the light-received signal output from said InGaAs light-receiving device at high speed when said object is being detected, wherein said optical system has a first reflecting surface which reflects the infrared rays for measurement and a second reflecting surface which reflects the infrared rays for reference, and wherein said first and second reflecting surfaces are disposed in a positional relationship so that the infrared rays reflected by said first and second reflecting surfaces are illuminated on said object with an optical axis of the infrared rays reflected by said first reflecting surface aligned with that of the infrared rays reflected by said second reflecting surface.

7. The infrared moisture measuring apparatus as set forth in 6, wherein said light-receiving device is a prism.

8. An infrared moisture measuring method which illuminates a measuring beam emitted from a first infrared light-emitting diode (LED) and a reference beam emitted from a second infrared LED to an object to be measured, also receives reflected beams of the measuring and reference beams with an InGaAs light-receiving device to obtain a moisture value of the object based on a light-received signal output from said InGaAs light-receiving device, and furthermore performs moisture-value display based on the obtained moisture value, the infrared moisture measuring method comprising the steps of:

operating said first and second infrared LEDs at high speed;

detecting a moisture value of the object by sampling said light-received signal of the InGaAs light-receiving device at high speed; and holding and displaying an average moisture value of the moisture values, measured when the measured moisture value is within a predetermined range, between the time that said measured moisture has gone out of said predetermined range and the time that said measured moisture has gone out of said predetermined range once again and thereby updating and displaying the average moisture value of each object to be measured.

9. An infrared moisture measuring method which illuminates a measuring beam emitted from a first infrared light-emitting diode (LED) and a reference beam emitted from a second infrared LED to an object to be measured, also receives reflected beams of the measuring and reference beams with an InGaAs light-receiving device to obtain a moisture value of the object based on a light-received signal output from said InGaAs light-receiving device, and furthermore performs moisture-value display based on the obtained moisture value, the infrared moisture measuring method comprising the steps of:

operating said first and second infrared LEDs at high speed;

detecting said object to be measured;

sampling said light-received signal of the InGaAs light-receiving device at high speed when said object is being detected;

intermittently measuring the moisture value of the object in correspondence with a detected state of the object; and     holding and displaying an average moisture value of the moisture values, measured when said object is detected and also a condition of the measured moisture value being within a predetermined range is satisfied, between the time that said condition is not longer satisfied and the time that said condition is no longer satisfied once again and thereby updating and displaying the average moisture value of each object to be measured.

10. An infrared moisture measuring method which illuminates a measuring beam emitted from a first infrared light-emitting diode (LED) and a reference beam emitted from a second infrared LED to an object to be measured, also receives reflected beams of the measuring and reference beams with an InGaAs light-receiving device through a lens, and furthermore obtains a moisture value of the object based on a light-received signal output from said InGaAs light-receiving device, the infrared moisture measuring method comprising the steps of:

operating said first and second infrared LEDs at high speed;

detecting said object to be measured;

sampling said light-received signal of the InGaAs light-receiving device at high speed when said object is being detected;

intermittently measuring the moisture value of the object in correspondence with a detected state of the object; and     determining an average moisture value of the moisture values, measured when the measured moisture value is within a predetermined range, between the time that said measured moisture value has gone out of said predetermined range and the time that said measured moisture value has gone out of said predetermined range once again.

11. The infrared moisture measuring method as set forth in claim 10, wherein optical axes of said measuring beam, said reference beam and said reflected beam are aligned with each other.

12. An infrared moisture measuring method which illuminates a measuring beam emitted from a first infrared light-emitting diode (LED) and a reference beam emitted from a second infrared LED to an object to be measured, also received reflected beams of the measuring and reference beams with an InGaAs light-receiving device through a lens to obtain a moisture value of the object based on a light-received signal output from said InGaAs light-receiving device, and furthermore performs moisture-value display based on the obtained moisture value, the infrared moisture measuring method comprising the steps of:

operating said first and second infrared LEDs at high speed;

detecting said object to be measured;

sampling said light-received signal of the InGaAs light-receiving device at high speed when said object is being detected;

intermittently measuring the moisture value of the object in correspondence with a detected state of the object; and     holding and displaying an average moisture value of the moisture values, measured while said object is being detected, between the time that said object is no longer detected and the time that the next object is no longer detected and thereby updating and displaying the average moisture value of each object,     wherein the step of holding and displaying further comprises the step of determining an average moisture value of the moisture values, measured when the measured moisture value is within a predetermined range, between the time that said measured moisture value has gone out of said predetermined range and the time that said measured moisture value has gone out of said predetermined range once again.

13. The infrared moisture measuring method as set forth in claim 12, wherein optical axes of said measuring beam, said reference beam and said reflected beam are aligned with each other.

\* \* \* \* \*